(12) United States Patent
Potthast et al.

(10) Patent No.: US 7,718,833 B2
(45) Date of Patent: May 18, 2010

(54) PURIFICATION OF GLYCERIN OBTAINED AS A BIOPRODUCT FROM THE TRANSESTERIFICATION OF TRIGLYCERIDES IN THE SYNTHESIS OF BIOFUEL

(75) Inventors: Rainer Potthast, Houston, TX (US);
Chi Ping Chung, Houston, TX (US);
Indresh Mathur, Sugar Land, TX (US)

(73) Assignee: Johann Haltermann, Ltd., Houston, TX (US)

( * ) Notice: Subject to any disclaimer, the term of this patent is extended or adjusted under 35 U.S.C. 154(b) by 1 day.

(21) Appl. No.: 12/290,728

(22) Filed: Nov. 3, 2008

(65) Prior Publication Data
US 2009/0137851 A1    May 28, 2009

Related U.S. Application Data

(60) Provisional application No. 61/001,530, filed on Nov. 2, 2007.

(51) Int. Cl.
*C07C 29/80* (2006.01)
*C07C 31/22* (2006.01)
*C07C 29/84* (2006.01)

(52) U.S. Cl. .................................................... 568/869
(58) Field of Classification Search .................. 568/869
See application file for complete search history.

(56) References Cited

U.S. PATENT DOCUMENTS

| 5,399,731 | A | 3/1995 | Wimmer |
| 6,015,440 | A | 1/2000 | Noureddini |
| 6,174,501 | B1 | 1/2001 | Noureddini |
| 6,262,285 | B1 | 7/2001 | McDonald |
| 7,126,032 | B1 | 10/2006 | Aiken |
| 7,138,536 | B2 | 11/2006 | Bournay et al. |
| 2007/0260078 | A1 | 11/2007 | Bhat et al. |
| 2007/0277430 | A1 | 12/2007 | Jackman et al. |
| 2007/0277432 | A1 | 12/2007 | Jackam et al. |
| 2008/0295392 | A1 | 12/2008 | Babello et al. |

*Primary Examiner*—Elvis O Price
(74) *Attorney, Agent, or Firm*—Butzel Long

(57) ABSTRACT

Methods for purifying glycerin contaminated with one or more lower boiling alcohols such as methanol, ethanol, straight, branched or cyclic C3-C6 alcohols, and the like. The methods are particularly useful for purifying crude glycerin phases recovered from the synthesis of biofuels. The present invention uses distillation techniques to strip alcohol contaminants from glycerin. In contrast to conventional methods that carry out distillation either under substantially anhydrous or very wet conditions, the present invention carries out distillation in the presence of a limited amount of water, e.g., from about 0.8 to about 5 parts by weight of water per 100 parts by weight of contaminated glycerin to be purified.

15 Claims, 2 Drawing Sheets

PURIFICATION OF GLYCERIN OBTAINED AS A BIOPRODUCT FROM THE TRANSESTERIFICATION OF TRIGLYCERIDES IN THE SYNTHESIS OF BIOFUEL

RELATED APPLICATIONS

The present application is based upon U.S. Provisional Application Ser. No. 61/001,530, filed Nov. 2, 2007 to which priority is claimed under 35 U.S.C. §120 and of which the entire disclosure is hereby expressly incorporated by reference.

FIELD OF THE INVENTION

The present invention relates to the purification of crude glycerin. More particularly, the present invention relates to the purification of crude glycerin recovered from the transesterification of triglycerides in the synthesis of biofuels.

BACKGROUND OF THE INVENTION

Biodiesel is a type of biofuel that is manufactured from triglycerides, diglycerides, and monoglycerides, but predominantly triglycerides. Vegetable oils, nut oils, animal fats, seed oils, fish oils, and the like are examples of suitable feedstocks containing triglycerides. In a typical synthesis, triglycerides are subjected to a transesterification reaction between the triglyceride and a stoichiometric excess of a suitable alcohol such as methanol, ethanol, or other linear, branched or cyclic C4, C5, or C6 alcohols. Use of ethanol and methanol are most common. The reaction occurs in the presence of a base catalyst and usually under substantially anhydrous conditions in which water is excluded as much as is practical. The reaction may be carried out in continuous or batch equipment.

The desired product of the transesterification is a fatty acid ester. When the alcohol reactant is methanol, this product is referred to as a fatty acid methyl ester, or FAME. The final contents of the reaction stream will also include glycerin (also known as glycerol) as a by-product alcohol; unreacted excess reactant alcohol; residual and spent catalyst (the spent catalyst may be present as a soap depending upon the catalyst used); and soaps present from fatty acids or other impurities that might have been present in the oil feedstock. The reaction usually proceeds far enough to completion that the amount of glyceride (whether mono, di, or tri) is de minimis.

The by-product glycerin is insoluble in the product ester to a large degree. Accordingly, the reaction stream separates into two phases as the transesterification reaction progresses. One phase is relatively rich in the fatty acid ester, while the other phase is relatively rich in glycerin. All of the constituents of the reaction vessel tend to be distributed among both phases, however. The glycerin layer is referred to herein as "crude glycerin". The other organic ingredients of the crude glycerin layer are referred to herein as contaminants with respect to the crude glycerin.

Glycerin itself is a triol having the formula $HOCH_2CH(OH)CH_2OH$ and has many uses. By way of example, it is used in medical and nutriceutical preparations, in personal care products, in foods and beverages, in animal feed, as a raw material to manufacture other compounds such as polyols and polyurethanes, in surface coatings and paints, in making absolute ethanol, in textiles, in de-icing fluids, in softeners and surfactants, in antifreeze, and the like. Accordingly, it is highly desirably to purify the crude glycerin inasmuch as glycerin has so many product uses. The methanol, fatty acid, and fatty acid ester contaminants in the crude glycerin also are valuable materials and are desirably recycled as well. For instance, the methanol, fatty acid, and the fatty acid ester can be recycled for use in further synthesis of biofuel or other products.

A key step in the purification of crude glycerin involves stripping the methanol from the crude glycerin using distillation techniques. Conventional methodologies have been problematic, however. In some instances, the distillation occurs under substantially anhydrous conditions. However, relatively high bottom temperatures must be used, e.g. temperatures above about 200° C., even above about 210° C., and even above about 220° C., in order to reduce the methanol content of the crude glycerin to acceptably low levels when distillation is anhydrous. At these temperatures, there is a substantial tendency for undue amounts of polyglycerin to form, undermining the goal to obtain purified glycerin. Temperature reduction by operation under vacuum to lower the temperatures requires a more sophisticated condenser/cooling system.

Carrying out wet distillation, however, is also problematic. Often, decanted wash water might be added to the crude glycerin in order to recover more fatty acid ester in an organic phase, which segregates as an upper layer on top of the glycerin. Methanol stripping from this or any other similarly wet layer is difficult due to excessive foaming caused by soap that is present. There is too much water, soap, and foaming for anti-foaming agents to help control this in any effective manner.

To attempt to avoid foaming, the crude, wet glycerin can be acidified to lower the pH to a value such as 2 to 5 in order to convert the soap into fatty acid. Still, the stripping of methanol from such acidic glycerin poses serious challenges due to corrosivity and reboiler plugging issues. First, the crude glycerin is corrosive due to its low pH, requiring equipment with expensive metallurgy for proper handling. Reboiler plugging can be caused by salts and the high distillation efforts to separate a dry methanol from such a wet glycerin. Reboiler plugging is a severe economic issue. The heat transfer coefficient decreases and the unit loses production capacity over time. Eventually, the unit will have to be shut down to remove salts by washing them out, by hydro blasting, or other suitable technique.

U.S. Pat. Nos. 6,262,285; 6,174,501; 7,126,032; and 7,138,536; as well as JP 10218810, discuss glycerin purification following biofuel synthesis.

There remains a strong need for effective methodologies that can purify crude glycerin, including aspects of this purification that involve separating crude glycerin from other alcohol contaminants such as methanol.

SUMMARY OF THE INVENTION

The present invention provides improved methods for purifying glycerin contaminated with one or more lower boiling alcohols such as methanol, ethanol, straight, branched or cyclic C3-C6 alcohols, and the like. The methods are particularly useful for purifying crude glycerin phases recovered from the synthesis of biofuels.

The present invention uses distillation techniques to strip alcohol contaminants from glycerin. In contrast to conventional methods that carry out distillation either under substantially anhydrous or very wet conditions, the present invention carries out distillation in the presence of a limited amount of water, e.g., from about 0.8 to about 5 parts by weight of water per 100 parts by weight of contaminated glycerin to be purified.

Several advantages result. Firstly, even though only a small amount of water is added, the addition drops the bottoms temperature significantly. For instance, when separating methanol from glycerin, using a limited amount of water allows the bottoms temperature to be under 200° C. and even under 190° C. at ambient pressure. This lower temperature as well as the impact of the water upon glycerin/polyglycerin equilibrium inhibits polyglycerin formation. The distillation is relatively easy due to the minimal amount of water that is present. The energy savings and throughput gains via improved reflux ratios are considerable. In short, using a limited amount of water avoids the major drawbacks associated with anhydrous distillation.

Using a limited amount of water also avoids the major drawbacks associated with wetter distillations. When only a limited amount of water is present, the soap remains soluble in the glycerin. Consequently, the small amount of water generates very little and even no foaming. The small amount of foaming that might be observed is easily handled with the addition of moderate amounts of anti-foaming agents, which is not the case with wetter distillations. Additionally, no salt deposits or reboiler plugging have been observed in the practice of many embodiments. Further, since corrosive acid need not be added to lower pH to control foaming, the distillation can occur in economical equipment such as that fabricated from mild/carbon steel. More expensive metallurgy is not required. The small amount of water also reduces the glycerin viscosity enough so that a subsequent phase separation between a glycerin phase and a FAME/FFA phase post-distillation, after acidification takes place with a sufficiently fast rate and completion. In many embodiments, the glycerin finally produced by this process typically has less than 1% of organic materials.

The performance is excellent. In representative modes in which methanol is stripped from crude glycerin recovered from biofuel synthesis, the crude glycerin has been assessed to include less than 500 ppm methanol after distillation. The stripped methanol is also highly pure, allowing it to be recycled.

After the methanol stripping, crude glycerin is easily separated from soap and fatty acid ester by an aqueous acid wash in representative embodiments. The wash yields an aqueous phase containing highly pure glycerin with low organic contaminant content and an organic phase with fatty acid/fatty acid ester that can be recycled for further processing or use, such as further biofuel synthesis.

In one aspect, the present invention relates to a method of purifying crude glycerin. An alkaline admixture (preferably one that is substantially anhydrous) comprising glycerin, soap, a fatty acid ester, and at least one other alcohol is provided. The other alcohol has a lower boiling point than glycerin. A sufficient amount of water is added to the admixture so that the admixture after adding the water includes from about 0.8 to about 5 parts by weight water per 100 parts by weight of the admixture. After adding the water, the admixture is distilled under conditions effective to strip away substantially all of the other alcohol. After stripping the other alcohol, the pH of the admixture is lowered with aqueous acid under conditions effective to convert the soap to free fatty acid and to form a first organic phase comprising the free fatty acid and the fatty acid ester and a second aqueous phase comprising the glycerin. The organic and aqueous phases are separated.

BRIEF DESCRIPTION OF THE DRAWINGS

The above mentioned and other advantages of the present invention, and the manner of attaining them, will become more apparent and the invention itself will be better understood by reference to the following description of the embodiments of the invention taken in conjunction with the accompanying drawings, wherein.

DETAILED DESCRIPTION OF PRESENTLY PREFERRED EMBODIMENTS

Figure 1:
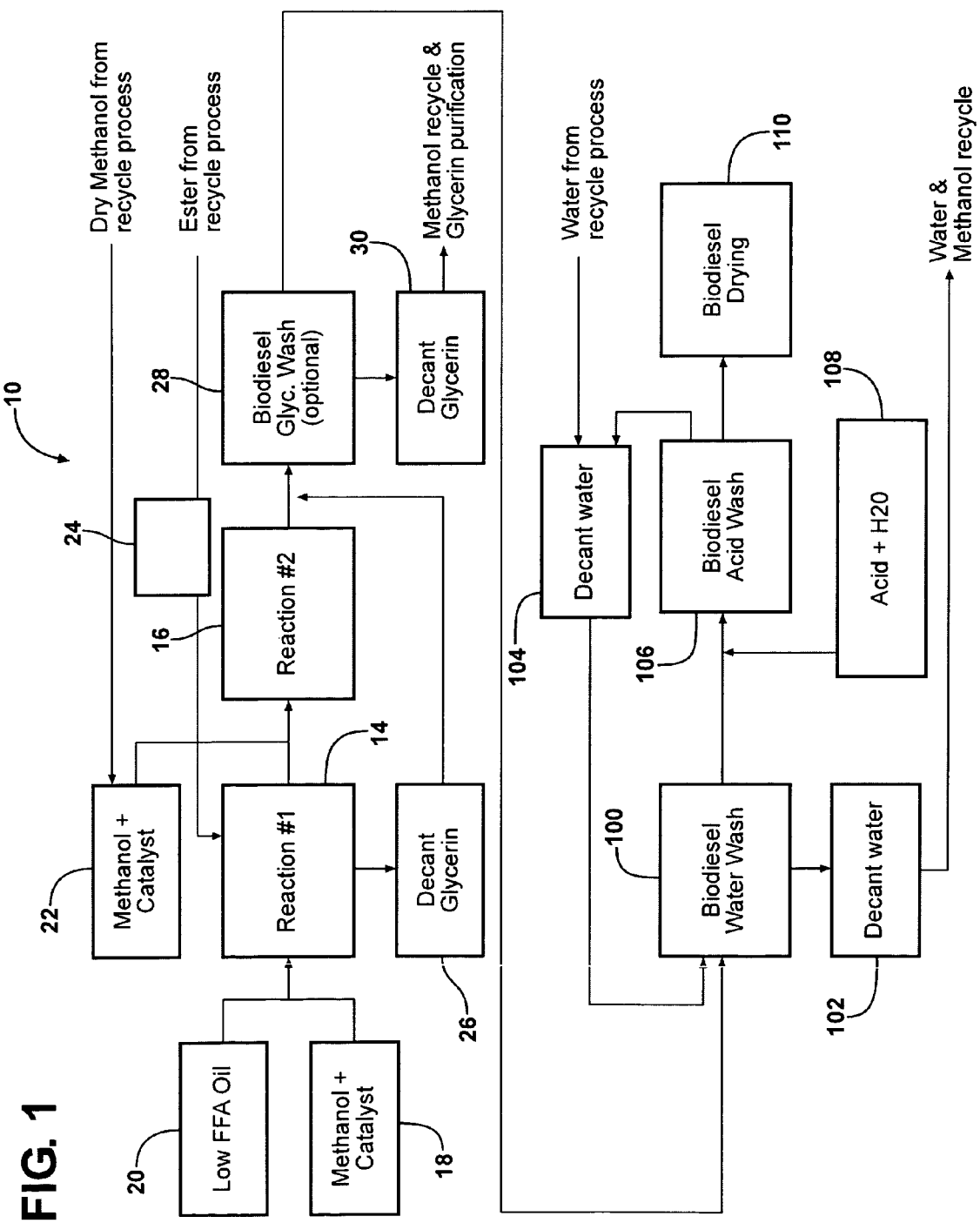
FIG. 1 is a schematic flow diagram showing how purification principles of the present invention are incorporated into a process for synthesizing a biofuel via the transesterification of triglycerides with methanol.

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

The present invention provides methodologies for separating glycerin (also known as glycerol) from contaminants including one or more other alcohol(s), at least one soap, and at least one fatty acid ester. The purification desirably occurs in two or more stages. In a first stage, the glycerin is separated from the one or more alcohols via distillation. Then, the glycerin is separated from the other contaminants in one or more additional stages. Because distillation techniques are desirably used to accomplish the removal of the one or more other alcohols, and because glycerin has a relatively high boiling point of about 290° C., the methodologies are particularly advantageously applied to alcohol contaminants having respective boiling points that are at least 30° C., desirably at least 60° C., and more desirably at least about 100° C. less than that of glycerin. These other alcohols may include one or more hydroxyl groups. The alcohol contaminants may be linear, branched, cyclic, fused, spyro, combinations of these, and/or the like. The one or more hydroxyl groups may be primary, secondary, or tertiary. In illustrative embodiments, alcohol contaminants include one or more of methanol, ethanol; linear or branched C3 alcohols; linear or branched C4 alcohols, linear or branched C5 alcohols, and/or the like. Methanol, ethanol, and/or C3 alcohols, often methanol, are contaminants encountered in crude glycerin resulting as a by-product in the synthesis of biofuels, as discussed further below.

The relative amount of alcohol contaminant(s) that can be removed from crude glycerin using techniques of the present invention can vary over a wide range, demonstrating the wide applicability of the present invention. In many representative, practical applications, the weight ratio of glycerin to other alcohol contamination may be in the range from about 1000:1 to 1:1000, sometimes 100:1 to 1:100; or sometimes 10:1 to 1:10. The invention can be applied to purify glycerin when the content of other alcohol contaminant(s) is outside these typical ranges, but these tend to be ranges that would be encountered most likely in actual practice. For example, crude glycerin resulting as a by-product from biofuel synthesis might have from about 10 to 90, 20 to 70, and sometimes 30 to 60 weight percent other alcohol(s), depending upon the amount of excess alcohol used as a reactant in the synthesis reaction.

The purification techniques of the invention allow not only the glycerin, but also the other alcohol(s) to be recovered with high purity.

According to preferred modes of practice, glycerin is distillingly separated from one or more, lower boiling alcohol contaminants in the presence of from about 0.8 to about 5, preferably from about 1 to about 4.5, more preferably from about 1.5 to about 4 parts by weight water is added per 100 parts by weight of the crude glycerin (not including the added water, but including other liquid phase contaminants that might be present in the crude glycerin such as soap(s), catalyst, spent catalyst, fatty acid ester, glycerides, and the like). The presence of a limited amount of water at the time of alcohol stripping is distinguished from conventional distillation procedures that occur under substantially more anhydrous or substantially more wet conditions. Whereas wet stripping tends to be difficult to due excessive foaming caused by soap contaminants that are typically present following biofuel synthesis, any soap tends has a greater tendency to stay dissolved in the glycerin when the water content of the distillation feed is limited. This dramatically reduces foaming and avoids having to resort to corrosive acid chemistries and expensive metallurgy to deal with foaming. If any foaming were to occur, it is so minimal as to be easily handled by adding only a minor amount of an anti-foaming agent such as Antifoam 2210 commercially available from Dow Corning. Using limited water also avoids the problems associated with reboiler plugging that follow from wetter distillations. The need to remove excessive amounts of water to further purify the glycerin is also entirely avoided.

On the other hand, using a limited amount of water also avoids the problems associated with substantially anhydrous stripping of alcohol contaminants from glycerin. Under substantially anhydrous conditions, distillation will tend to occur at higher temperatures, such as over 200° C. or even over 210° C. under ambient pressure and basic pH conditions. Under these conditions, substantial amounts of glycerin are converted to polyglycerin by-product, lowering the yield of glycerin recovery. The viscosity of the distillation bottoms also tends to be higher than might be desirable for easy handling. In contrast, with a limited amount of water, the alcohol stripping can more easily occur below 200° C., desirably below 190° C., even at a temperature of 170° C. to 180° C., under ambient pressure, when stripping an alcohol such as methanol from glycerin. In addition to lowering the boiling temperature, which inhibits polyglycerin formation, the presence of water also inhibits polyglycerin formation due to equilibrium effects. Generally, the distillation feed needs to be substantially anhydrous for polyglycerin to form. Even at low content according to the present invention, the water plays an important role as an intermediate boiling compound to ease the purification and avoid the production of polyglycerin by-products.

Significant other advantages result as well. The viscosity of the bottoms is dramatically lowered. Additionally, the reflux ratio of the distillation column drops considerably, improving both energy savings as well as throughput. For example, when stripping methanol from glycerin in the presence of 2 weight percent water leaving only 500 ppm methanol in the bottom in a column with 20 theoretical trays, the reflux ratio drops from 1.75:1 to 1.25:1. This improves energy savings and throughput by 20% for a given distillation unit. Any soap impurity, such as might be present from biofuel synthesis, remains soluble in the glycerin. De minimis if any salt deposits or reboiler plugging are observed. If a small amount of foaming does occur, it can easily be controlled by adding a small amount of an anti-foaming agent. This avoids antifoaming efforts that rely upon corrosive acid chemistries. As a consequence, distillation can occur in distillation equipment having ordinary metallurgy characteristics such as mild carbon steel as opposed to being limited only to more expensive, corrosion-resistant equipment.

Many alcohols other than methanol may tend to form azeotropes with water. Consequently, both water and alcohol may be removed when distillation occurs in the presence of such azeotropes. Under such circumstances, the azeotropic water that is removed or to be removed may be replenished in advance and/or as the water is taken out. At least a portion of this extra water could be added to the feed stream right away prior to distillation and/or a portion could be added at a suitable site such as to the reboiler or to the lower part of the distillation equipment being used.

The distillation may occur under a wide range of pressures including vacuum, partial vacuum, ambient pressure, or elevated pressure. On a commercial scale, the distillation occurs very effectively under ambient pressure, which is economical as well. Consequently, it can be appreciated that the distillation can be carried out in a wide range of distillation equipment, including those configured for batch or continuous processes.

The residual amount of alcohol contamination in the glycerin can be quite low. Distillation desirably is carried out under conditions so that the content of alcohol contaminant(s) remaining in the bottoms is less than 0.2%, desirably less than 0.1%, and more desirably less than 500 ppm. The stripped alcohol also desirably is highly pure as well. In typical embodiments, the stripped alcohol includes less than 500 ppm glycerin. Methanol, which does not form an azeotrope with water, includes less than 1000 ppm, preferably less than 500 ppm, more preferably less than 300 ppm water on a weight basis.

The principles of the present invention can be incorporated into more complex purification systems in which glycerin is separated from a combination of contaminants including not only one or more other alcohols but also other materials such as fatty acids, fatty acids esters, soaps, catalysts, spent catalysts, combinations of these and the like. For purposes of illustration, these aspects of the invention will be described in the context of purifying crude glycerin generated as a by-product in the synthesis of biofuels. Such crude glycerin results as a by-product of the transesterification of glycerides with an alcohol.

In a typical transesterification process, a glyceride is reacted with excess alcohol in the presence of a base catalyst. Vegetable oils, nut oils, animal fats, seed oils, fish oils, and the like are examples of suitable feed stocks containing glycerides. Examples of oils include rapeseed oil, sunflower oil, safflower oil, soybean oil, coconut oil, gourd oil, corn oil, cottonseed oil, canola oil, olive oil, palm oil, peanut oil, sesame oil, almond oil, cashew oil, hazelnut oil, macadamia oil, pecan oil, pistachio oil, walnut oil, tung oil, castor oil, coconut oil, hemp oil, mustard oil, combinations of these, and the like. These oils often include triglycerides, but also may contain some amount of monoglyceride and diglyceride. The glycerides are mono, di, and tri esters of glycerin with a fatty acid. Some free fatty acid may also be present in these oils, but suppliers often reduce the fatty acid content by stripping to less than 1%, or even less than 0.5% by weight. Lower fatty acid content is desirable. Alternatively, oils with higher amounts of fatty acid like Yellow Grease (recycled oil from restaurants) or Jatropha oil, as well as recycle methylester from the biodiesel synthesis process, are often pre-esterified with glycerin or the alcohol to be used in a transesterification.

The alcohol reactant can be selected from any one or more alcohols that undergo alcoholysis substitution exchange reaction with the glyceride material to transesterify the reactants into glycerin and fatty acid esters. Representative examples of alcohols include methanol, ethanol, propyl alcohol, isopropyl alcohol, linear and branched C4 alcohols, and the like. Methanol is often preferred in this reaction to produce a fatty acid methyl ester (FAME) product.

The stoichiometric excess of alcohol used can vary over a wide range. As general guidelines, it is desirable to use enough of the alcohol so that the reaction products phase separate into two liquid layers. Often, using 170% to 300%, more desirably about 200% of the theoretical, stoichiometric amount of alcohol can be used for reactions carried out at suitable temperatures, such as from about 15° C. to being heated up under pressure to way above 100° C. in order to get the reaction done in just a few seconds or even faster. This generally may correspond to using from about 7 to about 40 weight percent of alcohol based upon the weight of the oil used.

The transesterification reaction is catalyzed by bases such as potassium hydroxide, sodium hydroxide, sodium methoxide, potassium methoxide, sodium ethoxide, sodium methylate, potassium methylate, sodium ethylate, potassium ethylate, combinations of these, and the like. The catalyst may be used in any amount effective to catalytically facilitate the transesterification reaction at least to some degree. In typical embodiments, using from about 0.1 to about 2 weight percent of catalyst based upon the weight of the oil would be suitable. Prior to introducing the alcohol to the reaction vessel, the catalyst is often pre-mixed with the alcohol.

Thus, the transesterification reaction desirably occurs by mixing the feedstock of glyceride and the pre-mix of alcohol and catalyst in a suitable reaction equipment for a suitable time period. If the reactor has a headspace, this may optionally be blanketed with an inert gas such as nitrogen, argon, carbon dioxide, or the like. Carrying out the reaction in clean dry air is possible, but oxygen may cause peroxides and other undesirable oxygenated products to form, specifically with the double bonds that are present in many unsaturated oil compounds.

However, the reaction desirably occurs under as anhydrous conditions as is practically feasible. Desirably, the water content of the mix is less than 0.1 weight percent, and more desirably under 0.05 weight percent. If desired, the reaction can occur under pressure or under vacuum, although ambient pressure is suitable as well.

As the reaction proceeds, the contents of the reactor will tend to phase separate into two liquid layers. The top layer is a FAME-rich layer, while the bottom layer is a glycerin-rich layer. In addition to FAME, the FAME-rich layer will also include some glycerin, left-over alcohol, soap (spent catalyst as well as soap resulting from free fatty acid in the oil feedstock, for instance), catalyst, and sometimes a very minor amount of water. The glycerin-rich phase, also referred to as crude glycerin, also will include some FAME, left-over alcohol, soap (spent catalyst as well as soap resulting from free fatty acid in the oil feedstock, for instance), catalyst, and sometimes a very minor amount of water. The glycerin-rich phase can be separated from the FAME-rich phase by any suitable method, such as decanting, and then purified in accordance with principles of the present invention. One example of a purification system for purifying the crude glycerin will be described below in connection with FIGS. 1 and 2.

Although the transesterification reaction is an equilibrium reaction, the fact that the reaction product glycerin tends to separate into a separate phase helps to drive the equilibrium toward completion since the products of the reaction are removed from the reaction environment as a practical matter due to the phase separation. However, because the catalyst generally prefers to be in the crude glycerin phase, the reaction will tend to slow down as more glycerin is made. Accordingly, it may be desirable to carry out the reaction in two or more stages. In a first stage, the reaction is allowed to proceed until the rate slows down too much so that a desired residence time would be exceeded. The crude glycerin phase is then decanted or otherwise removed from the reaction stream. Fresh catalyst is added to the reactor, optionally pre-mixed with additional alcohol reactant, and the reaction is allowed to proceed further. After a time period, the additional crude glycerin is removed from the reactor and may be combined with the crude glycerin from the first stage for purification treatment. Often, two stages are sufficient for the reaction to proceed very far to completion, e.g., 99% or more, but one or more additional stages can be performed if further reaction progress is desired.

The reaction time will depend upon factors including the temperature, pressure, amount of catalyst, amount of alcohol relative to the oil, intensity of initial mixing and the like.

The reactor may include features that allow the reactor contents to be mixed or otherwise agitated during the course of the reaction. The reactor may also be fitted with features, such as a jacket or the like, that allows the reactor to be heated or cooled to desired temperature(s).

Conditions for carrying out the transesterification reaction are described in the patent and technical literature, including documents such as U.S. Pat. Nos. 5,424,467; 6,262,285; 6,174,501; 7,126,032; and 7,138,536; as well as JP 10218810; and also Peterson, C. L., Feldman, M., Korus, R., and Auld, D. L. (1991), "Batch Type Transesterification Process for Winter Rape Oils" Applied Engineering in Agriculture, 7(6) pp. 711-716 and "Process Development of Rapeseed Oil Ethyl Ester as a Diesel Fuel Substitute" M.S. Thesis by Narendra Bam, University of Idaho, July, 1991.

The crude glycerin collected from the one or more stages of reaction advantageously may be purified using procedures of the present invention. In a first purification step, the alcohol reactant, often methanol or ethanol, is stripped from the crude glycerin using distillation techniques as described above. Because the crude glycerin collected from the transesterification step tends to be substantially anhydrous, typically including less than about 0.5 weight percent water, enough water is added to help ensure that the distillation can occur at a temperature below 200° C., desirably below 190° C. and even below 180° C. Preferably, enough water is added so that the distillation feed includes 0.8 to about 5, preferably from about 1 to about 4.5, more preferably from about 1.5 to about 4 parts by weight water per 100 parts by weight of the crude glycerin (not including the added water) being distilled for the reasons discussed above.

In carrying out this distillation, the pH is preferably sufficiently high to ensure that the soap content of the crude glycerin is soluble in the glycerin and remains in the form of soap. If the pH were to be too low, corrosion becomes a main concern. As collected from the transesterification reaction, the pH of the glycerin will be at a suitable alkaline pH to carry out the distillation, e.g., a pH of about 10 or more, even about 12 in some embodiments. Optionally, although not required, the pH can be lowered prior to distillation to make the crude glycerin less alkaline (e.g., 8 to 10), more neutral (e.g., 7 to 8) or even moderately acidic so long as the soap is not converted to an insoluble fatty acid ester in a way that would unduly compromise the effectiveness of the alcohol stripping.

Distillation is carried out until the alcohol contaminant level in the crude glycerin is reduced to desired levels within practical limits. By way of example, one mode of practice can reduce the methanol content in crude glycerin to less than 0.2 weight percent, even less than 500 ppm, based upon the total weight of the crude glycerin (including the limited amount of water in the crude glycerin for this calculation) from a crude glycerin including one weight percent water at the start of the distillation. This distillation was carried out at about 180° C. at 760 mmHg and is described further in the examples below. The stripped alcohol also tends to be sufficiently pure that it may be recycled and used for desired purposes, including being recycled for participation in further biofuel transesterification reactions.

After the distillation, the remaining crude glycerin will still include contaminants including soap, fatty acid ester(s), catalyst, and the limited amount of water added to ease the distillation phase of the purification. The next phase of the purification separates the glycerin from these other organic contaminants, any of which also can be recycled optionally after further purification or other handling. One way to accomplish the separation of the glycerin from the other organics is to wash the crude glycerin with an acidic water wash. This converts the soap(s) to free fatty acid(s). The mixture also phase separates into a an aqueous, glycerin-rich phase with very low organic contaminant content and a separate organic phase containing organic materials including the fatty acid(s), fatty acid ester(s), and the like. In practical effect, the acid water wash incorporates a chemical reaction that converts some contaminants to a form more amenable to separation from the glycerin as well as a liquid-liquid extraction to isolate the glycerin from other organic constituents of the crude glycerin. Note with this approach that the addition of water and acid is delayed until after the excess alcohol reactant(s) in the crude glycerin have been stripped out via the prior distillation phase of purification.

The pH desirably is lowered sufficiently to convert the soap content to fatty acids. In many embodiments, lowering the pH to a range from about 3 to about 5, preferably about 3 to about 4, is suitable. Lower pH targets could be used, but this would require more acid than is required to achieve the desired goal of converting the soap to fatty acids. A wide range of acids can be used to lower the pH to the desired range. Strong mineral acids such as HCl or $H_2SO_4$ or strong organic acids such as citric acid are preferred. Using either concentrated or dilute forms of these acids would be suitable. However, when the amount of water that can be present in the glycerin-rich phase is subject to a specification that limits the amount of water in that phase (e.g., one specification might specify a maximum of 18 weight percent water in the phase based upon the total phase weight), using a concentrated acid is often desirable to avoid a risk of adding to much water. It follows that any amount of water may be added as desired, subject to satisfying water specifications that might be applicable. When a water specification applies, the amount of water added is calculated so that the glycerin-rich phase will be within the specification after phase separation.

Either acid or water may be added to the crude glycerin, or the two ingredients can be added together. For commercial scale processes, it is desirable to add the water first, and then the acid. The admixture desirably is mixed throughout acid addition for a sufficient period of time at suitable temperature(s) to allow the conversion of soap to fatty acid to occur. By way of example, the admixture is mixed for a time period in the range from about 3 minutes to 72 hours, preferably 30 minutes to 48 hours, more preferably 1 hour to 24 hours at a temperature in the range from above about 0° C. to about 95° C., preferably about 20° C. to about 70° C., more preferably about 35° C. to about 60° C. In one embodiment, the reaction took place at 50° C. for about 18 hours. When the admixture is allowed to settle after the reaction, a top organic layer containing fatty acid esters and free fatty acid separates relatively quickly from a bottom, aqueous, glycerin-rich layer in the presence of the added water. After the layers are separated, the pH of the glycerin layer may be raised so as to be mildly acidic (e.g., from about 5 to about 6) or neutralized (from about 6 to about 8) by addition of a suitable base such as NaOH, KOH, and/or the like. The material in the upper layer may be recycled such as being recycled for conversion to biofuel.

The resultant glycerin may be highly pure with respect to organic contaminants. Embodiments have yielded glycerin at this stage in which the organic content is less than 1 weight percent and even less than 0.5 weight percent based upon the total weight of the contained glycerin. This indicates that the stripping of alcohol contaminants first in the presence of limited water, followed by the acidic water wash removes contaminants including other alcohols, fatty acid, and fatty acid ester from glycerin very effectively.

Figure 2:
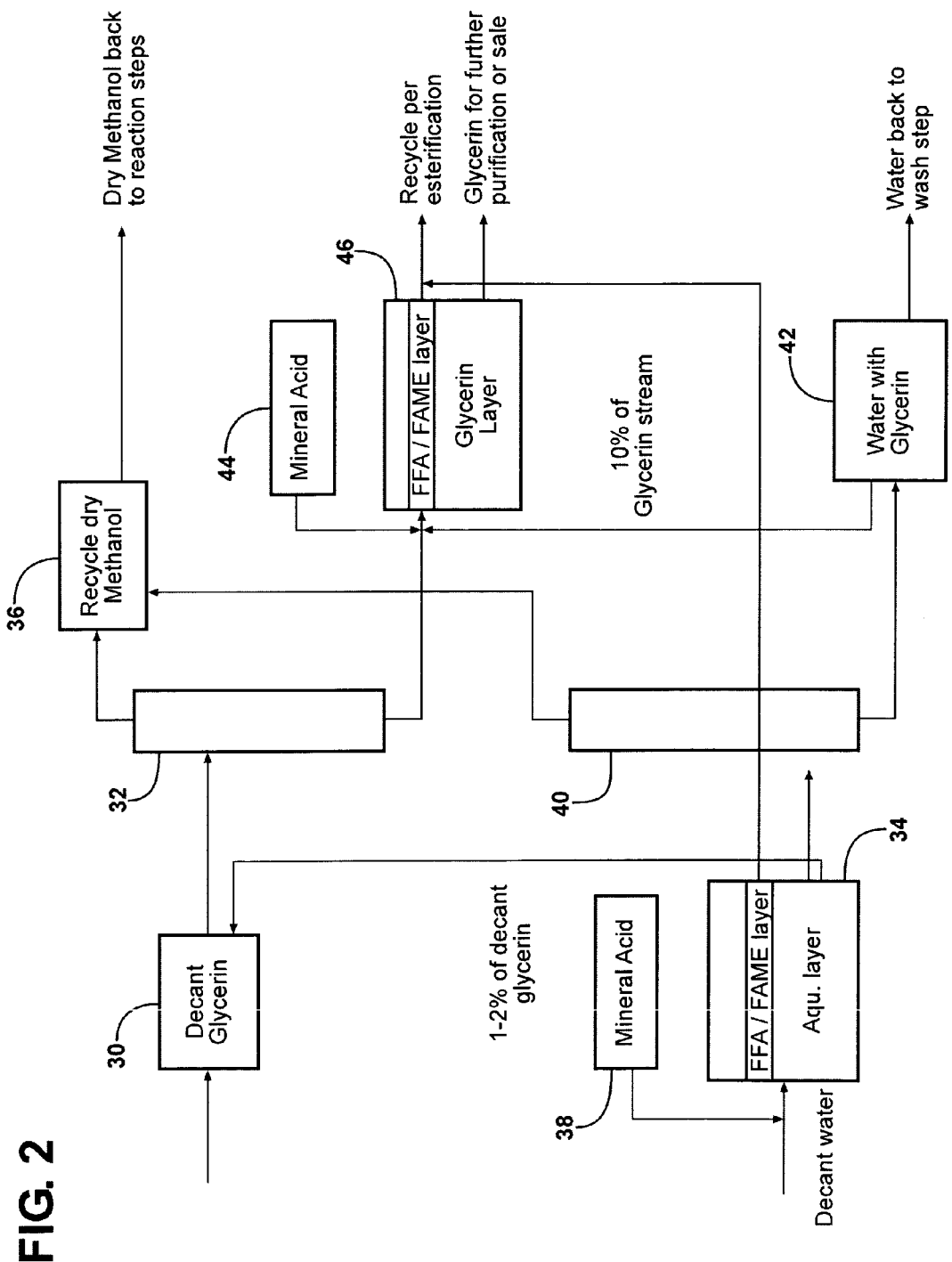
FIG. 2 is a schematic flow diagram showing how crude glycerin recovered in the biofuel synthesis process of FIG. 1 is purified using principles of the present invention.

FIGS. 1 and 2 schematically show an illustrative biofuel synthesis scheme 10 incorporating a glycerin purification system 12 of the present invention. Referring first mainly to FIG. 1, the reactants used to carry out the transesterification reaction, shown occurring in two stages 14 and 16 are fed to a suitable reactor vessel. These reactants include a fresh supply of alcohol and catalyst from source 18 as well as one or more oil feed stocks from source(s) 20. For purposes of illustration, source 18 provides a premix of methanol and catalyst, while source 20 provides a low FFA (free fatty acid content less than 1 weight percent, even less than 0.5 weight percent) vegetable oil. Additionally, recycled methanol and catalyst recovered by system 12 is also fed to the reactor vessel from supply 22. Recycled fatty acid ester recovered by system 12 may also be fed to the reactor vessel from supply 24. The recycled supplies 22 and 24 may be fed to the reactor vessel to supply either the first reaction stage 14 or the second reaction stage 16. For purposes of illustration, the recycled methanol and catalyst from supply 22 is added to the reactor vessel to carry out the second reaction stage 16 after the first reaction stage is complete, while the recycled fatty acid ester from supply 24 is added to the reactor vessel as part of the feed to carry out the first reaction stage 14.

When the reactants are fed to the reactor vessel, the reactor contents tend to phase separate into a fatty acid ester rich layer and a crude glycerin layer as the transesterification reaction proceeds. As mentioned above, however, the catalyst tends to be more soluble in the glycerin phase than in the fatty acid ester phase, which also tends to include most of the triglyceride material. Thus, reaction tends to slow down as more crude glycerin forms. Accordingly, to conclude the first reaction stage 14, the crude glycerin is decanted from the reactor vessel as shown by step 26. Fresh methanol and catalyst from supply 22 are then added to carry out the second reaction stage 16. When this reaction is complete, the decanted glycerin of step 26 is used to wash the reactor contents at step 28. As a consequence of this wash, the reactor contents phase separate into a fatty acid ester rich layer and a crude glycerin layer. The fatty acid ester rich layer, for which the fatty acid ester will be used as a constituent of biodiesel, is carried forward to step 100 for purification, as will be described further below. The crude glycerin layer resulting from the wash is decanted at step 30 (shown on both FIGS. 1 and 2) and then carried forward to purification system 12.

Purification system 12 is shown in more detail in FIG. 2. As a first step, the decanted glycerin from step 30 is combined with a limited amount of water so that the resulting admixture includes from about 0.8 to about 5, preferably from about 1 to about 4.5, more preferably from about 1.5 to about 4 weight percent water based upon the weight of the decanted crude glycerin to which the water is to be added. The water can come from a fresh source. Alternatively, as shown, the water can come from the aqueous layer that phase separates in the acid water wash of step 34. The resulting decanted, crude glycerin including the limited amount of water is then subjected to distillation in step 32 in order to strip the methanol. The resultant dry methanol 36 can be recycled as shown and used as a source for the methanol and catalyst supply 22 (see FIG. 1).

In the meantime, decanted aqueous phase from decanting step 102 of FIG. 1 is combined with a mineral acid from source 38 of FIG. 2 to carry out the phase separation in step 34. The decanted aqueous phase of step 102 prior to the addition of this acid is highly alkaline and will tend to include not only water, but also glycerin, methanol, soap, and fatty acid ester (FAME). It is desirable to remove the soap (which is converted to free fatty acid, FFA) and FAME from this decanted water before using the water further. To accomplish this, enough of the mineral acid is added to lower the pH to a range at which the soap is converted to free fatty acid. In step 34, the admixture then separates into an aqueous phase including mainly water, glycerin, and methanol and an organic phase including mainly free fatty acid and fatty acid ester, specifically FAME. The organic layer can be used for recycle, being a source of feedstock for supply 24 of FIG. 1.

The aqueous phase resulting from step 34 is subjected to a distillation in step 40 to separate the methanol from the water and glycerin. The methanol resulting from this distillation is combined with the methanol recovered from the distillation of step 32. The water with a minor amount of glycerin is recycled in two ways. As shown by step 42, a portion of the water with glycerin is used in supply 104 to carry out a water wash of the biodiesel in step 100 (FIG. 1), while another portion is used along with mineral acid to subject the crude glycerin from distillation step 32 to an acid water wash. Thus, mineral acid from supply 44, the crude glycerin from the distillation step 32, and the water with glycerin from step 42 are combined to conduct an acid water wash of the crude glycerin in step 46. The acid water wash is carried out according to the protocols described above. An exemplary embodiment is also described in the Examples, below. In step 46, the soap in the crude glycerin is converted to free fatty acid (FFA). The FFA and the FAME separate into an organic, top phase, while the water and glycerin separate into a bottom, aqueous phase. The purified, aqueous glycerin resulting from step 46 can be sold, further purified to separate the glycerin from water, or otherwise processed or handled as desired. The FFA/FAME layer can be used as a source of feedstock for supply 24 (FIG. 1).

Referring again to FIG. 1, the purification of the biofuel resulting from step 28 will now be described in more detail. In step 100, the biofuel obtained from step 28 is washed with water. The water is obtained from supply 104, using recycled water from step 42 as a feedstock. The admixture of step 100 separates into an organic phase containing purified FAME (e.g., 98% pure in illustrative embodiments) and an aqueous phase. The aqueous phase is decanted in step 102 and used as the source water for step 34 in FIG. 2. The water from supply 104 is mildly acidic, but the overall admixture in step 100 will be alkaline due to the strong alkalinity of the biofuel obtained from step 28.

Next, the FAME phase from step 100 is subjected to an aqueous acid wash in step 106. This wash helps to remove metal impurities as well as converting residual soap into tolerable amounts of fatty acid. Excess strong acid remains in the aqueous layer, which is decanted or otherwise separated, e.g., by centrifuge. The aqueous acid is obtained from source 108. A wide range of acids may be used. Strong mineral or organic acids such as HCl, $H_2SO_4$, citric acid, phosphoric acid, combinations of these, and the like may be used in dilute or concentrated form. The resultant admixture separates into an organic phase include the FAME and an aqueous phase. The aqueous phase can be recycled and used as part of the supply 104. The FAME phase can be further processed or otherwise handled in one or more subsequent steps. For purposes of illustration, the FAME is next dried in step 110, and then is ready for use or distribution.

The present invention will now be described with reference to the following illustrative examples.

EXAMPLE 1

This example uses principles of the present invention to remove MeOH from crude glycerin using distillation in the presence of a limited amount of water. The crude glycerin treated in this example was the glycerin bottom obtained from the transesterification of soybean oil with methanol. This crude glycerin had the following characteristics:

TABLE 1

| | |
|---|---|
| pH | 12 |
| Water (wt. % by K.F.)* | 0.26 |
| Composition, wt % | |
| MeOH | 47.5 |
| Glycerin | 41.1 |
| Esters | 11.3 |
| Soap, ppm as Na-oleate by titration | 112000 |

*K.F. refers to Karl Fischer titration according to ASTM D789.

The limited amount of water makes the methanol removal easier (compared to a wetter glycerin distillation by avoiding excessive foaming (foaming requires water). Additionally, if too much water were to have been present during distillation the soap present in the crude glycerin could cause coking and plugging around the reboiler.

Continuous distillation was used to strip the methanol from the crude glycerin. For purposes of this example, it was desired that the methanol content in the purified glycerin be no more than 0.2% by weight. As preparation for the distillation, ChemCAD simulation indicated that in order to meet glycerin's max 0.2% MeOH spec the bottom temperature would be >220° C. at 760 mmHg if the distillation were to be carried out under substantially anhydrous conditions. However, this temperature would be high enough to create an undue risk of significant polyglycerin formation or other decomposition reactions. However, by adding 1% water to the feed (based upon the total weight of the crude glycerin), the simulation showed the bottom temperature could be lowered to ~180° C. at 760 mmHg and still produce the bottom with MeOH in the desired specification. Therefore, 1% DI water was added to the crude glycerin for this example. A moderate head reflux was applied so the MeOH could meet the water spec. The following tables summarize the distillation parameters:

TABLE 2

| | |
|---|---|
| Column | 3 section Sulzer packing column, total ~30 stages. |
| Head pressure | 760 mmHg |
| Diff. pressure | 1 mmHg |
| Feed point | Above sec. 1 |
| Head reflux | 1:1.5 |
| Feed rate | 500 g/hr @60° C. |
| Head flow | 245 g/hr (49.0% yield) |
| Btm | 255 g/hr (51.0% yield) |

TABLE 3

Column temperature profile, ° C.

| | |
|---|---|
| Head | 64 |
| Sec. 2 | 64 |
| Sec. 1 | 65 |
| Btm | 189 |

TABLE 4

Stream composition:

| | Head | Btm |
|---|---|---|
| Color, APHA | <10 | |
| Water, % by K.F. | 0.02 | 1.5 |
| MeOH, % | 99.30 | 0.44 |
| Glycerin, % | 0.03 | 76.5 |
| Esters, % | 0 | 21.5 |
| Others, % | 0.65 | — |

With 1% water added to the feed, the bottom temperature was kept at about 190° C., well below 200° C. The recovered MeOH included only 0.02 weight percent water and, thus, could be recycled for biodiesel transesterification. There was no precipitation or coking observed in the reboiler. No soap precipitated out at room temp., however, the material was quite viscous. On a commercial scale, it might be good to add water to this bottom stream right at the after cooler to lower the viscosity and ease handling. Some foaming was observed in the reboiler. Dow corning Antifoam 2210 worked very well to break the foam.

EXAMPLE 2

This example describes further purification of the crude glycerin processed in accordance with Example 1. After the MeOH was removed from the crude glycerin, the glycerin had a pH of 12 and still contained soap and methyl esters. By acidifying the crude glycerin, the soap could be converted into FFA. The FFA and FAME (fatty acid methyl ester) could be separated from the glycerin and recycled. For this example, a specification was applied in which the recovered, purified glycerin would include a maximum of 18 weight percent water based on the total weight of glycerin and water.

In order to convert the sodium salt of fatty acids (i.e., the soap) to free fatty acid, the crude glycerin acidified to pH 3-4. $H_2SO_4$ was added slowly into the glycerin until pH ~3.5. Overall, 2.7 weight percent $H_2SO_4$ (98%) was used. After the acid was added, 14% by weight water was added as well based on the weight of the crude glycerin. The reaction took place at 50° C. for ~18 hours. The amount of water used was calculated so that the glycerin bottom, after FFA and FAME separation, would meet the max 18% water specification. In this example, acid was added first, followed by addition of water. The order of this addition can be reversed. For example, the water may be added first to reduce viscosity before the acid is added. However, if the addition of water initiates foaming in the mixing process, then the acid desirably is added first to convert the foam-causing soap into fatty acid. It was observed that the consistency of the acidified glycerin changed from viscous fluid at the beginning to gel like material and to liquid again after fatty acid was formed. Due to the presence of water, layers developed with an upper FAME/FFA layer and a lower water/glycerin layer. The composition of each of the layers was analyzed as follows:

TABLE 5

| | Upper layer | Btm layer |
|---|---|---|
| Water, % by K.F. | 0.2 | 16.9 |
| Composition, % by | | |
| GC* | | |
| Glycerin | 3.9 | 99.6 |
| Esters + FFA | 94.1 | 0.1 |
| Others | 2.0 | 0.2 |
| FFA, % by titration | 74.6 | — |

*GC refers to gas chromatography.

Analysis showed that the glycerin layer included less than 0.3 weight percent of other organics. This is well within a typical industry specification such as one that requires a maximum of 1% by weight of other organics (sometimes expressed as a maximum of 1% M.O.N.G., wherein the term "M.O.N.G." is an abbreviation for matters organic non-glycerin, an English translation of a French expression). This indicates, that the removal of methanol, followed by water/acid addition removes methanol and then the FFA/FAME quite efficiently. At end, the glycerin pH was adjusted to 6 by NaOH addition.

In a follow up, the upper layer of FAME/FFA was successfully recycled and converted to biodiesel.

EXAMPLE 3

A limited amount of water is added to a crude glycerin feedstock obtained from the synthesis of biodiesel having to provide an admixture having the following range of characteristics:

| | |
|---|---|
| Water | 1-3% |
| Soap, as Sodium Oleate | 15-25% |
| FAME | 1-5% |
| Methanol | 15-30% |
| Glycerin | 45-65% |
| pH | 10-12 |

The admixture is then distilled to strip methanol. The distillation is done in either mild steel or stainless steel units of 3-6 ft diameter at either atmospheric pressure or moderate overpressure or vacuum. Feed enters the column at or below the middle of the distillation tower. At the head, a Methanol stream with 500 ppm water is recovered. This dry methanol is fit for reuse in a biodiesel synthesis process.

The bottom temperature ranges between 160° C. and 190° C. depending mostly upon the amount of added water. A glycerin stream is taken from the bottom. This stream contained a maximum of 0.5% by weight Methanol. Despite the high amount of soap present, the stream is substantially homogenous. The glycerin is acidified to a pH of 2-4 while the stream is still warm to allow the quick removal of a FFA/

FAME layer by decantation or centrifugation. No reboiler fouling, coking or decomposition resulted from the distillation. Very moderate foaming was kept under control by an antifoam agent (Dow Corning 2210) injection to the feedstock as needed.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of purifying crude glycerin, comprising the steps of:
    a) providing an alkaline admixture comprising glycerin, soap, a fatty acid ester, and at least one other alcohol, said other alcohol having a lower boiling point than glycerin;
    b) adding a sufficient amount of water so that the admixture includes from about 0.8 to about 5 parts by weight water per 100 parts by weight of the admixture;
    c) after adding the water, distilling the admixture under conditions effective to strip away substantially all of the other alcohol;
    d) after stripping the other alcohol, lowering the pH of the admixture with aqueous acid under conditions effective to convert the soap to free fatty acid and to form a first organic phase comprising the free fatty acid and the fatty acid ester and a second aqueous phase comprising the glycerin; and
    e) separating the organic and aqueous phases.

2. The method of claim 1, wherein step (b) comprises adding from 1 to 4.5 parts by weight of water per 100 parts by weight of the admixture.

3. The method of claim 1, wherein the other alcohol is selected from methanol, ethanol, and linear, branched or cyclic C3 to C6 alcohols.

4. The method of claim 3, wherein the other alcohol is methanol.

5. The method of claim 1, wherein the fatty acid ester is a fatty acid methyl ester.

6. The method of claim 1, wherein the aqueous acid is selected from HCl, $H_2SO_4$, phosphoric, and citric acid.

7. The method of claim 1, wherein step (b) comprises lowering the pH to a value in the range from about 2 to about 4.

8. The method of claim 1, further comprising the step of adding an antifoaming agent to the admixture while step (c) is being carried out.

9. The method of claim 1, wherein the distillation occurs at a pressure of about 760 mmHg.

10. The method of claim 1, wherein enough water is added so that the distillation occurs at a temperature of less than 200° C. in order to reduce the amount of the other alcohol to less than 1 weight percent.

11. The method of claim 10, wherein enough water is added so that the distillation occurs at a temperature of less than 190° C. in order to reduce the amount of the other alcohol to less than 1 weight percent.

12. The method of claim 1, wherein the admixture has an alkaline pH during at least a portion of step (c).

13. The method of claim 12, wherein the pH is 10-13.

14. The method of claim 13, wherein the pH is about 12.

15. The method of claim 1, wherein the admixture of step (a) is substantially anhydrous.

* * * * *